United States Patent [19]
Balloul et al.

[11] Patent Number: 5,753,236
[45] Date of Patent: May 19, 1998

[54] **ANTIGENIC COMPOSITION OBTAINED BY V8 PROTEOLYSIS OF A PROTEIN FROM *S. MANSONI***

[75] Inventors: Jean-Marc Balloul, Lille; Raymond Pierce, Seclin; Jean-Marie Grzych, Marcq en Baroeul; André Capron, Phalempin, all of France

[73] Assignees: Institut Pasteur, Paris Cedex; Institut Pasteur de Lille, Lille, both of France

[21] Appl. No.: 438,564

[22] Filed: May 10, 1995

Related U.S. Application Data

[60] Continuation of Ser. No. 135,533, Oct. 14, 1993, abandoned, which is a division of Ser. No. 836,725, Feb. 19, 1992, Pat. No. 5,279,822, which is a division of Ser. No. 681,468, Apr. 4, 1991, abandoned, which is a continuation of Ser. No. 492,358, Mar. 9, 1990, abandoned, which is a continuation of Ser. No. 69,989, Jul. 6, 1987, abandoned.

[30] Foreign Application Priority Data

Jul. 3, 1986 [FR] France ................... 8609663

[51] Int. Cl.⁶ .............. A61K 39/02; A61K 39/002; C07K 16/00; C12P 21/08
[52] U.S. Cl. .............. 424/266.1; 424/184.1; 424/265.1; 530/350; 530/388.1; 530/388.2; 530/388.6; 435/69.3; 435/68.1
[58] Field of Search ............... 424/184.1, 265.1, 424/266.1; 530/350, 388.1, 388.2, 388.6, 266.1; 435/69.3, 68.1

[56] References Cited

U.S. PATENT DOCUMENTS 5,279,822  1/1994  Balloul et al. .

OTHER PUBLICATIONS

Balloul et al. Mol. Bioch. Parasit. 17:105–114, 1985.
Cleveland et al. J. Biol. Chem. 252(3):1102–06, 1977.
Vignali et al. Immunol Today 1012):410–416, 1989.
Shes et al. Parasitology 98 Suppl.:S61–S68, 1989.
Scott et al. Immunol Rev. 112:161–182, 1989.
Huqeunel et al, FASEBJ. 44(3):654 Abstract M26, 1985.
Harn et al. 1985. Mol. Biochem. Parasitology. 16:345–54.
Aron 1991. Vaccine. 9:379–94.

*Primary Examiner*—Paula K. Hutzell
*Assistant Examiner*—N. M. Minnifield
*Attorney, Agent, or Firm*—Oblon, Spivak, McClelland, Maier & Neustadt, P.C.

[57] ABSTRACT

An antigenic composition against *S. mansoni* comprising an 8 kD peptidic fragment associated with a suitable vehicle, the 8 kD peptidic fragment being obtained by controlled proteolysis using V8 protease of a 28 kD protein obtained from *S. mansoni* is described.

4 Claims, 2 Drawing Sheets

ANTIGENIC COMPOSITION OBTAINED BY V8 PROTEOLYSIS OF A PROTEIN FROM S. MANSONI

This application is a Continuation of application Ser. No. 08/135,533, filed on Oct. 14, 1993, now abandoned, which is a division of application Ser. No. 07/836,725, filed Feb. 19, 1992, now U.S. Pat. No. 5,279,822, which is a division of application Ser. No. 07/681,468, filed Apr. 4, 1991, now abandoned, which is a continuation of application Ser. No. 07/492,358, filed Mar. 9, 1990, abandoned, which is a continuation of application Ser. No. 07/069,989, filed Jul. 6, 1987, abandoned.

BACKGROUND OF THE INVENTION

The present invention relates to a peptide isolated from the 28 KD protein of S. mansoni, which bears one or more epitopes and to its process of isolation, as well as to monoclonal antibodies adapted to recognize the peptidic antigenic fractions thus isolated and to therapeutic compositions adapted to induce neutralizing anti-body synthesis, which compositions comprise said peptide alone or in association with other suitable substances.

BALLOUL et Al. (MOLECULAR AND BIOCHEMICAL PARASITOLOGY, 17 (1985) p. 105–114) described the synthesis in vitro of an antigen constituted by a polypeptide having a molecular weight of 28 KD and an isoelectric point comprised between 6.3 and 6.8, which constitutes a translation product in vitro of total RNA of Schistosoma mansoni.

The above Authors have pursued their research with the object of isolating from this polypeptide of 28 KD and of identifying, the peptidic epitope or epitopes responsible for the antigenic properties.

It is known to analyze the peptides which constitute proteins isolated from SDS gels, by partial digestion of said proteins by a protease in a buffer containing SDS; stable partial digestion products are obtained, which are composed of numerous peptides whose molecular weights are sufficiently high for it to be possible to separate them on 15% SDS acrylamide gels CLEVELAND et Al., THE JOURNAL OF BIOLOGICAL CHEMISTRY, 252, p. 1102–1106, (1977)).

Applicants have sought to isolate, from the 28 KD protein of S. mansoni, the one or more peptides bearing the anti-Schistosoma antigenic activity shown by the 28 KD, protein, and have made use for this purpose of techniques for isolating peptidic fragments by proteolysis described in the prior art.

GENERAL DESCRIPTION OF THE INVENTION

Figure 1:
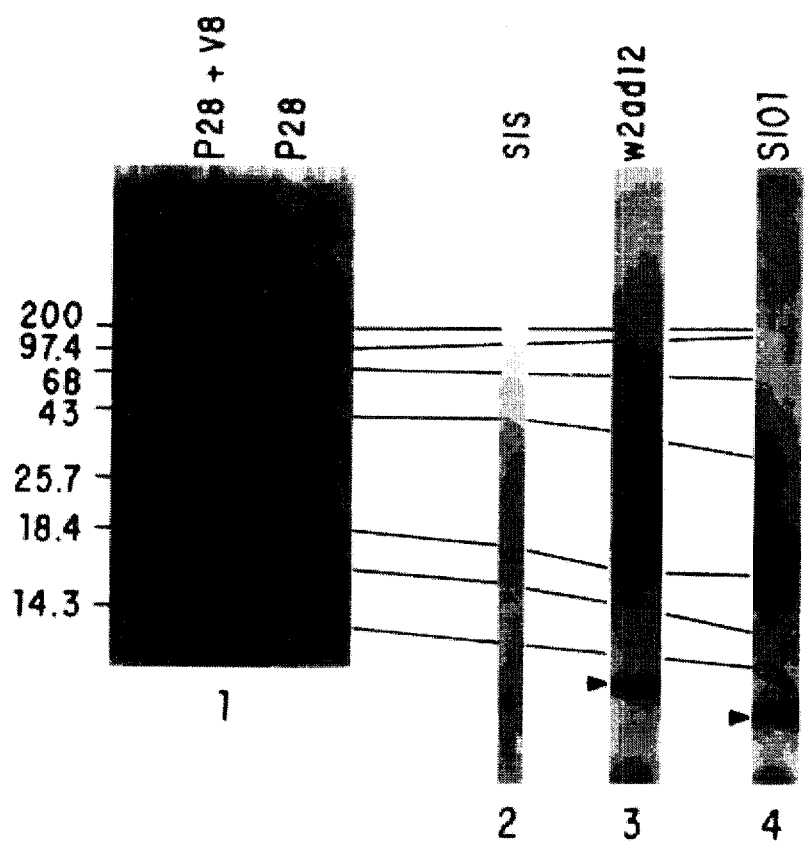
FIG. 1 illustrates a Western blot having four blocks in which:
a. block 1 exhibits in the lower portion thereof the peptide isolated by proteolysis, and at the upper portion thereof the 28 KD protein of the present invention;
b. block 2 exhibits the blot obtained with serum of a healthy rabbit;
c. block 3 represents the blot obtained with monoclonal antibodies obtained from hybridoma W2 AD 12; and
d. block 4 represents the blot obtained with polyclonal rabbit anti-28 kD serum.

It is an object of the present invention to provide a process for isolating a peptide bearing at least one epitope, by proteolysis, characterized in that the 28 KD protein of S. mansoni is subjected to the action of V8 protease in Tris-HCl buffer pH 6.8 containing SDS, in that the proteolysis reaction is stopped by the addition of a mixture of 2-mercaptoethanol and SDS, then it is brought to boiling at 100° C. for a short time, to collect a peptide of which the antigenic activity is checked by means of antibodies of a polyclonal serum or of monoclonal antibodies.

In a preferred embodiment of the process according to the present invention, the enzymatic digestion of the 28 KD protein by the VE protease is performed for 30 minutes at 30° C.

In another preferred embodiment of the process according to the present invention, the mixture used to stop the proteolysis reaction comprises 2-mercaptoethanol in the proportion of 1 µl per 3 µl 10% SDS.

In yet another preferred embodiment of the process according to the present invention, the Tris-HCl buffer in which the 28 KD protein is dissolved is a buffer 100 mM to 125 mM and contains 0.08 to 0.12% of SDS.

In another preferred embodiment of the process according to the invention, the checking of the antigenic activity of the peptide isolated by proteolysis, which is done by Western blotting by means of a anti-28 KD polyclonal serum of rat, rabbit or the like, reveals, by means of antibodies labelled with peroxidase, directed against immunoglobulins of rat, rabbit, mouse or the like, a 6 KD peptidic epitope.

In yet another preferred embodiment of the process according to the invention, the checking of the antigenic activity of the peptide isolated by proteolysis, which is done by Western blotting by means of an anti-28 KD monoclonal antibody reveals a peptidic epitope of 8 KD.

It is also an object of the present invention to provide a peptidic fragment, characterized in that it is isolated from the 28 KD protein of S. mansoni by controlled proteolysis, in that it has a molecular weight of 6 KD and in that it is recognized by anti-28 KD polyclonal serum of rabbit, of rat or the like.

It is also an object of the present invention to provide a peptidic fragment, characterized in that it is isolated from the 28 KD protein of S. mansoni by controlled proteolysis, in that it has a molecular weight of 8 KD and in that it is recognized by an anti-28 KD monoclonal antibody, of isotype IgG2a (W 2 AD 12).

Moreover the present invention has the object of providing a hybridoma named M 5 BD 9, which provides IgM isotype monoclonal antibodies which recognize the 28 kD antigen.

It is also an object of the present invention to provide a hybridoma named W 2 AD 12, deposited at the CNCM on 9 May 1986 under No. I-553, which provides monoclonal antibodies of IgG2a isotype which recognize a strip corresponding to a peptidic fragment of 8 KD, isolated by controlled proteolysis of the 28 KD polypeptide of S. mansoni.

According to the present invention, the hybridomas M 5 BD 9 and W 2 AD 12 are obtained by proceding as follows:
Monoclonal antibodies directed against the group of 28 kD proteins of Schistosoma mansoni were obtained by rat×rat homologous cell hybridization using the myelomatous strain of rat LOUIR983F (Bazin et Coll. 1980 Ann Immunol. (Institut Pasteur) 131 D: 359), and spleen cultures of LOU rat immunized with 50 μg of the 28 kD group of proteins of *S. mansoni*, in the presence of complete Freund adjuvant, in two subcutaneous injections of 25 μg, at 15-day intervals.

After fusion, the anti-28 kD antibody-producing cells were selected by radioimmunological tests on plates. A homogenate of adult worms is fixed to polyvinyl plates, then contacted with the anti-bodies present in the supernatants of the hybrid cultures. The antigen-antibody linkage is then revealed by the addition of a second anti-body labelled with iodine $^{125}I$, directed against rat IgGs. The positive cells in this test were cloned by the method of limiting dilution.

It is in addition an object of the present invention to provide a vaccinating composition against *S mansoni* which is characterized in that it contains at least one peptide fragment of 28 KD of *S. mansoni* isolated by controlled proteolysis, associated with a suitable vehicle.

In an advantageous embodiment of the vaccinating composition according to the present invention, the latter contains at least one peptide fragment of 6 KD and/or of 8 KD associated with a suitable vehicle.

In another advantageous embodiment of the vaccinating composition according to the present invention, the latter contains at least one peptide fragment of 28 KD of *S. mansoni* isolated by controlled proteolysis, associated with the epitope of the 38 KD antigen, as well as with a suitable vehicle.

The epitope of the antigen of MW 38 KD is an oligosaccharide which forms the subject of French Patent Application No. 86 06281 of 30 Apr. 1986 in the name of Applicants.

Besides the foregoing features, the invention comprises other features, which will emerge from the description which follows.

The invention will be better understood by means of an example of performing the process according to the present invention and examples of characterization of the antigenic activity of the peptide according to the invention.

It must however be well understood that this example of its practice, is given purely by way of illustration of the invention, of which it does not constitute in any way a limitation thereof.

DESCRIPTION OF PREFERRED EMBODIMENTS

EXAMPLE 1
PREPARATION OF THE PEPTIDE ISOLATED FROM THE 28 KD PROTEIN OF *S. mansoni*

Step 1: Preparation of the antigen of 28 KD of *S. mansoni*

*S. mansoni* adult worms (Porto Rican strain) collected by perfusion of the portal vein in golden hamsters, were homogenized in a PBS buffer in a POTTER-ELVEHSEM homogenizer and the homogenisate was centrifuged at 5000 rpm for 20 minutes.

About 2 mg of antigens were fractionated on 13% polyacrylamide gels in plates, by using the batchwise buffer system of Laermmi (described by LAEMMLI, NATURE (1970), 227, p. 680–685).

After electrophoresis, the gels were dyed with COO-MASSIE Brilliant Blue. The dyed strips were cut up with a scalpel and transferred into an elution gel constituted by castings of support gel.

Elution was performed at 40–60 V for 6 to 12 hours. The speed of elution is a function of the percentage of the gel separated and the molecular size of the proteins that are eluted. Migration of the samples was stopped at the interface of the layers of 2M NaCl-glycerol. When all the peptides had been eluted into the glycerol layer, the electrophoresis was stopped and the samples were withdrawn by means of a PASTEUR pipette. The samples were then dialyzed against water to remove the SDS and the salts, before being concentrated by freeze-drying. The fractionated proteins were then reanalyzed on 13% polyacrylamide gel, in a plate.

The protein of MW 28 KD obtained by the fractionation technique which has just been described, and which is characterized in that it induces an anti-body response and in that its antiserum immunoprecipitates the corresponding 28 KD antigens among the in vitro translation products both of RNA of adult worms and RNA of Schistosomulas of *S. mansoni*, is taken for processing according to Step II below.

Step II: Isolation by proteolysis of a peptide of the protein 28 KD of *S. mansoni*

10 μg of protein of 28 KD are dissolved in 30 μl of 125 mM Tris-HCL buffer (pH 6.8) containing 0.1% of sodium dodecysulfate (SDS).

1 μg of protease V8 is added and the enzymatic digestion of the antigen of 28 KD is performed at 37° C. for 30 minutes, on the water bath.

The reaction is stopped by the addition of 1 μl of 2-mercaptoethanol and 3 μl of 10S SDS. The whole is brought to 100° C. on the water bath for 6 minutes.

Specimens constituted by a peptide of which the antigenic properties are determined, were collected

EXAMPLE 2
ANALYSIS OF THE ANTIGENIC RESPONSE OF THE PEPTIDE OF EXAMPLE 1

10 μg of the peptide obtained in Example 1 were deposited on a 20% polyacrylamide gel. The peptide so-fractionated was transferred onto a nitrocellulose sheet as described by TOWBIN et Al. (1984, J. Immunol. Methods 72, p. 471).

The nitrocellulose sheet was first saturated with a 3% BSA solution buffered by mono- and disodium, phosphate 10 mM pH 7.2 containing 0.15M NaCl-50 μl of antibodies, which antibodies were either antibodies of a polyclonal serum of rat or of rabbit or monoclonal ascites antibodies, or antibodies obtained from a hybridoma, specifically from hybridoma W 2 AD 12, M 5 BD 9.

Antigen and antibody are left in contact overnight at room temperature, to obtain a "Western blot" which is washed three times for thirty minutes in phosphate buffer.

Antibodies labelled with peroxidase (supplied by PASTEUR PRODUCTION) directed either against rabbit immunoglobulins (in the case of polyclonal antibodies) or against rat immunoglobulins (in the case of monoclonal antibodies), were then added and incubated with the "blot" for 2 hours. Three further washings were carried out and the presence of immunocomplexes was revealed by the addition of a solution containing 20% of cold methanol, 30 mg of 4-chloro-1-naphthol, 0.1% of $H_2O_2$ per 100 ml of phosphate buffer, 0.15M NaCl.

The western blotting is shown in FIG. 1 attached in which:

block 1 shows in its lower portion the peptide isolated by proteolysis, according to the invention and at its upper portion the protein 28 KD ;

block 2 represents the "blot" obtained with a healthy rabbit serum;

block 3 represents the "blot" obtained with mono-clonal antibodies coming from the hybridoma W 2 Ad 12;

block 4 represents the "blot" obtained with poly-clonal rabbit anti-28 KD serum.

This Western blotting shows that the monoclonal antibody W 2 AD 12 bearing a cytotoxic activity with respect to the post-infecting larvae of Schistosorma mansoni recognized a fragment of 8 kD derived from the protein of 28 kD.

The recognition by an antibody of anaphylactic class suggests the importance of this peptide in the induction of a protective response with respect to *S. mansoni*.

The epitope borne by a fragment of 6 kD recognized by the rabbit serum is not recognized by the rat mono-clonal antibody suggesting that the recognition of this or that epitope of the 28 kDa antigen is specific as to species.

EXAMPLE 3
CHECKING OF THE RECOGNITION OF THE ANTIGENIC PEPTIDE ACCORDING TO THE PRESENT INVENTION WITH MONOCLONAL ANTIBODIES

A. Search for a peptidic epitope of restricted size among the proteolysis products of the 28 KD antigen, enabled a fragment of 8 KD to be revealed recognized specifically by the monoclonal antibody of isotype IgG2a, obtained from the hybridoma W 2 AD 12. The cytotoxic activity (illustrated in Table 1 below) of this monoclonal antibody in vitro tests involving eosinophils, suggests the importance of the one or more epitopes borne by this peptide of 8 KD.

TABLE 1

Eosinophil-dependent Cytotoxicity

| Source of antibodies[a] | Percentage of cyto-[b] toxicity ± S.D. |
|---|---|
| Serum of rat carrying the hybrid subcutaneous tumor W 2 AD 12 | 66.9 ± 26.0 |
| Serum of rat carrying the subcutaneous tumor of IR983F cells | 7.3 ± 1.06 |
| Serum of rat immunized by protein 28 kD | 69.9 ± 22.9 |
| Serum of rat infected for 4 weeks with S. mansoni | 74.3 ± 23.5 |
| Serum of healthy rat | 5.0 ± 4.2 |

The cytotoxicity tests were carried out according to the conditions described by Capron et Coll. (Eur. J. Immunol., 8, 127–133, 1975).

a) The schistosomulas were presensitized during 18 hours, in the presence of 100 μl of different serums (final dilution 1/16) heated 1 hour at 56° C., b) Percentage cytotoxicity (mean±standard deviation from the mean) was measured after 48 hours of incubation of the schistosomulas sensitized in the presence of peritoneal cells from healthy rats (ratio effective cells/target=6000/1).

The anti-28 KD rabbit serum did not recognize the one or more epitopes borne by this peptide, but recognized another peptide, of 6 KD. The monoclonal antibody of W 2 AD 12 recognized the two peptides of the group of antigens of 28 KD.

B. monoclonal antibody of IgM, isotype obtained from the hybridoma M 5 BD 9 only recognized one of two proteins of the 28 kD group.

Figure 2:
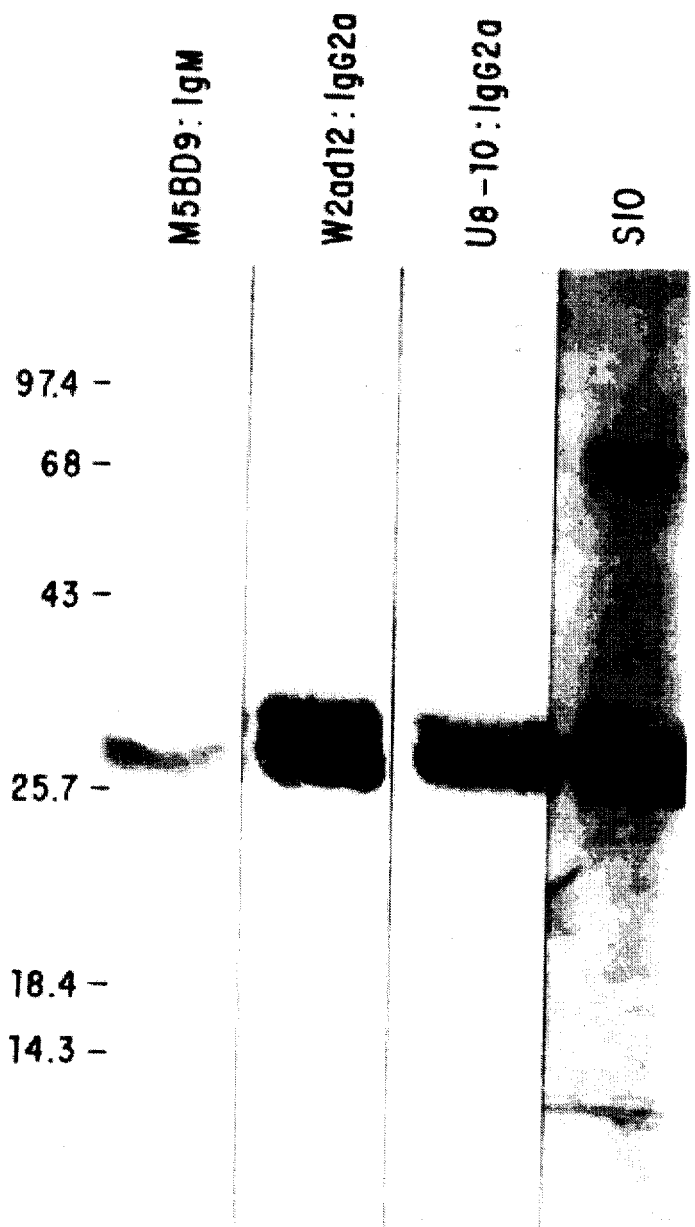
FIG. 2 illustrates a Western blot of a group of antigens of the 28 kD protein of the present invention using monoclonal antibodies.

FIG. 2 attached shows the results of Western blotting of the group of antigens of 28 kD according the invention with monoclonal antibodies of M 5 BD 9, W 2 AD 12 and with polyclonal rabbit serum such as described above.

We claim:

1. An antigenic composition for a mammal against *S. mansoni*, which comprises a peptidic fragment of 8 kD associated with a suitable vehicle, said 8kD fragment reacting with a cytotoxic antibody W2AD12 (deposited at the CNCM as No. I-553) and being obtained by controlled proteolysis of a 28kD protein isolated from *S. mansoni*, the controlled proteolysis comprising:

a) subjecting the 28kD protein of *S. mansoni* to proteolysis by V8 protease in Tris-HCl buffer containing SDS to produce an 8kD fragment, b) stopping the proteolysis reaction by adding thereto a mixture of 2-mercaptoethanol in SDS, and boiling at 100° C. for a time sufficient to stop proteolysis, and c) collecting said 8kD peptide.

2. The antigenic composition of claim 1, wherein the said enzymatic digestion of said 28kD protein by said V8 protease is effected for about 30 minutes at 30° C.

3. The antigenic composition of claim 1, wherein said mixture used to stop said proteolysis reaction comprises 2-mercaptoethanol in a proportion of 1 μl for 3 μl of 10% SDS.

4. The antigenic composition of claim 1, wherein said Tris-HCl buffer in which said 28kD protein is dissolved is a buffer of 100 mM to 125 mM and contains 0.08 to 0.12% of SDS.

* * * * *